US010048268B2

(12) United States Patent
Kitahara et al.

(10) Patent No.: US 10,048,268 B2
(45) Date of Patent: Aug. 14, 2018

(54) LATEX PARTICLE FOR MEASUREMENT REAGENT, COATED LATEX PARTICLE, AND MEASUREMENT REAGENT FOR IMMUNOTURBIDIMETRIC METHOD

(75) Inventors: Shinichiro Kitahara, Ibaraki (JP); Yuki Takahashi, Ibaraki (JP)

(73) Assignee: SEKISUI MEDICAL CO., LTD., Tokyo (JP)

(*) Notice: Subject to any disclaimer, the term of this patent is extended or adjusted under 35 U.S.C. 154(b) by 1085 days.

(21) Appl. No.: 14/008,168

(22) PCT Filed: Mar. 30, 2012

(86) PCT No.: PCT/JP2012/058590
§ 371 (c)(1),
(2), (4) Date: Nov. 20, 2013

(87) PCT Pub. No.: WO2012/133771
PCT Pub. Date: Oct. 4, 2012

(65) Prior Publication Data
US 2014/0065726 A1 Mar. 6, 2014

(30) Foreign Application Priority Data

Mar. 31, 2011 (JP) ................. 2011-080374

(51) Int. Cl.
C08L 25/18 (2006.01)
C08L 71/00 (2006.01)
G01N 33/58 (2006.01)
C08F 212/08 (2006.01)
G01N 33/543 (2006.01)
G01N 33/53 (2006.01)

(52) U.S. Cl.
CPC ......... *G01N 33/585* (2013.01); *C08F 212/08* (2013.01); *G01N 33/54313* (2013.01)

(58) Field of Classification Search
CPC ........ C08F 212/08; C08F 2/26; C08F 212/32; C08F 212/14; G01N 33/54313; G01N 33/585
See application file for complete search history.

(56) References Cited

U.S. PATENT DOCUMENTS

| 7,338,813 B2* | 3/2008 | Obana ................ C08F 212/08 428/403 |
| 2004/0171176 A1 | 9/2004 | Obana |
| 2009/0117596 A1 | 5/2009 | Hashimoto et al. |
| 2014/0377881 A1* | 12/2014 | Kitahara ............... C08F 212/08 436/501 |

FOREIGN PATENT DOCUMENTS

| CN | 101273270 | 9/2008 |
| CN | 102128924 | 7/2011 |
| EP | 0 597 510 | 5/1994 |
| JP | 58-76762 | 5/1983 |
| JP | 2001-296299 | 10/2001 |
| WO | 03/005031 | 1/2003 |

OTHER PUBLICATIONS

Niushijima, Y. Fluorescence methods in polymer science. J. Polymer Sci. 1970, No. 31, pp. 353-373.*
Govindaiah et al. Monodisperse and fluorescent poly(styrene-co-methacrylic acid-co-2-naphthyl methacrylate)/Fe3O4 composite particles. Journal of Colloid and Interface Science 2010, vol. 343, pp. 484-490.*
Kim et al. Emulsifier-free emulsion copolymerization of styrene and sodium styrene sulfonate. J. Polymer Sci. 1992, vol. 30, pp. 171-183.*
Office Action dated Aug. 24, 2015 in corresponding European patent application No. 12 765 483.8.

* cited by examiner

*Primary Examiner* — Shafiqul Haq
(74) *Attorney, Agent, or Firm* — Wenderoth, Lind & Ponack, L.L.P.

(57) ABSTRACT

An object of the present invention is to provide a latex particle for a measurement reagent with which highly sensitive measurement can be performed even in measuring a measurement sample containing a test substance in a dilute concentration.
The preset invention relates to a latex particle for a measurement reagent including a copolymer obtained by copolymerizing a monomer mixture containing the following polymerizable monomers (a) to (c):
 (a) a polymerizable monomer having a phenyl group;
 (b) a polymerizable monomer having a phenyl group and a sulfonate; and
 (c) a polymerizable monomer having a naphthyl group, in an aqueous medium containing 7.5 to 25% by weight of $C_{1-4}$ alcohol without using a surfactant.

6 Claims, 2 Drawing Sheets (a)

(b)

LATEX PARTICLE FOR MEASUREMENT REAGENT, COATED LATEX PARTICLE, AND MEASUREMENT REAGENT FOR IMMUNOTURBIDIMETRIC METHOD

TECHNICAL FIELD

The present invention relates to a latex particle for a measurement reagent with which highly sensitive measurement can be performed even in measuring a measurement sample containing a test substance in a dilute concentration.

BACKGROUND ART

In a variety of fields including the field of clinical laboratory test, immunological measurement methods utilizing antigen-antibody reactions are widely used as a method for quantitatively determining a trace test substance contained in a measurement sample. Especially, latex immunoturbidimetric method using latex particles as a carrier for an antigen or an antibody is simply operated and takes a short period of time for the measurement. Therefore, the number of kinds of trace test substances to be measured by employing the latex immunoturbidimetric method as a measuring method is further increasing.

For quantitatively determining a test substance of an antigen, an antibody or the like contained in a measurement sample by the latex immunoturbidimetric method, change in absorbance caused by aggregation of latex particles carrying the antigen or the antibody (hereinafter sometimes referred to as "coated latex particles") is optically detected. This change in absorbance is on the basis of change in apparent particle sizes of aggregates formed by the aggregation of the coated latex particles.

As the latex particles used as a carrier in the latex immunoturbidimetric method, polystyrene latex particles containing polystyrene as a principal component have been conventionally used because antigen- or antibody-coating (immobilization) is easy, they are comparatively inexpensive and they can be easily controlled in the polymerization reaction (Patent Literature 1 and the like). In the case where polystyrene latex particles are used as a carrier in the latex immunoturbidimetric method, however, if the concentration of a test substance in a measurement sample is dilute, then the number of aggregates to be formed is small, and the apparent particle sizes of the aggregates are also small as compared with the case where the concentration of the test substance relative to the number of latex particles falls within an appropriate range, resulting in a disadvantageously insufficient sensitivity.

Accordingly, in order to improve the measurement sensitivity that is lowered when the concentration of a test substance is dilute, an attempt has been made to increase the particle size of the polystyrene latex particles so as to increase the apparent particle size of aggregates to be formed.

When the particle size of the latex particles is too large, however, it is necessary to make adjustment by decreasing the concentration of coated latex particles in a reaction solution to be applicable to an optical measuring device to be used, because of the upper limit of the absorbance measurable by the optical measuring device. Lowering the concentration of coated latex particles in a reaction solution reduced the probability of the coated latex particles encountering with the test substance within a certain period of time, and measurements without the expected improvement in the sensitivity were often experienced. Moreover, when the particle size of the latex particles working as a carrier is increased, the latex particles are liable to precipitate, and hence, if a measurement reagent containing the coated latex particles is stored in the form of a solution, the storage stability is degraded.

In this manner, when the method in which the particle size of the polystyrene latex particles is increased is employed, although the improvement in the measurement sensitivity can be expected up to a given particle size, if the particle size is increased beyond the given size, there arise problems in which the measurement sensitivity is degraded on the contrary and the storage stability of the measurement reagent is degraded.

As a countermeasure, Patent Literature 2 discloses a method for improving the measurement sensitivity by increasing the refractive index of latex particles without increasing the particle size thereof. Even when the latex particles described in Patent Literature 2 are used, however, there still arises a problem in which expected measurement sensitivity cannot be actually attained.

CITATION LIST

Patent Literature

Patent Literature 1: International Publication No. WO2003/005031
Patent Literature 2: JP 2001-296299 A

SUMMARY OF INVENTION

Technical Problem

An object of the present invention is to provide a latex particle for a measurement reagent with which highly sensitive measurement can be performed even in measuring a measurement sample containing a test substance in a dilute concentration.

Solution to Problem

The present invention relates to a latex particle for a measurement reagent containing a copolymer obtained by copolymerizing a monomer mixture comprising the following polymerizable monomers (a) to (c):

(a) a polymerizable monomer having a phenyl group:
(b) a polymerizable monomer having a phenyl group and a sulfonate; and
(c) a polymerizable monomer having a naphthyl group,
in an aqueous medium containing 7.5 to 25% by weight of $C_{1-4}$ alcohol without using a surfactant.

The present invention will now be described in detail.

The present inventors have investigated the reason why the expected measurement sensitivity is not attained by the latex immunoturbidimetric method using coated latex particles prepared by using the latex particles described in Patent Literature 2. As a result, it has been found that the cause is a surfactant contained in the latex particles. In the method described in Patent Literature 2, a surfactant is used as an emulsifier for producing latex particles having a high refractive index in a state having a uniform particle size. This surfactant remains in the latex particles, resulting in that the surfactant inhibits the antigen- or antibody-coating (immobilization) on the surfaces of the latex particles. Therefore, the amount of the antigen or the antibody adsorbed onto the latex particles is insufficient, which is probably the reason why measurement sensitivity as high as expected is not attained.

The present inventors have found, as a result of earnest studies, the following: When a latex particle comprising a copolymer obtained by copolymerizing, without using a surfactant, a monomer mixture comprising specific polymerizable monomers is used, even if its particle size is equivalent to that of the conventional polystyrene latex particle, a latex particle for a measurement reagent with which highly sensitive measurement can be performed even in measuring a measurement sample containing a test substance in a dilute concentration can be obtained. Thus, the present invention has been accomplished.

The latex particle for a measurement reagent of the present invention comprises a copolymer obtained by copolymerizing, without using a surfactant, a monomer mixture comprising the following polymerizable monomers (a) to (c).

Furthermore, a latex particle for a measurement reagent comprising a copolymer having segments derived from the following polymerizable monomers (a) to (c) and comprising no surfactant is another aspect of the present invention:
(a) a polymerizable monomer having a phenyl group;
(b) a polymerizable monomer having a phenyl group and a sulfonate; and
(c) a polymerizable monomer having a naphthyl group.

The polymerizable monomer having a phenyl group (a) is not especially limited, and examples include styrene, o-methyl styrene, p-methyl styrene, p-chlorostyrene, 4-vinylbenzoate, divinylbenzene and vinyl toluene. One of these polymerizable monomers may be singly used or two or more of them may be used in combination. Among these, styrene is preferably used.

The content of the polymerizable monomer having a phenyl group (a) in the monomer mixture has a lower limit of preferably 40 mol % and an upper limit of preferably 94.9 mol %. If the content of the polymerizable monomer having a phenyl group (a) is less than 40 mol %, a particle size distribution may become wide in some cases, and if the content exceeds 94.9 mol %, the content of the polymerizable monomer having a naphthyl group (c) in the monomer mixture may be too small to attain high sensitivity in some cases. The lower limit of the content of the polymerizable monomer having a phenyl group (a) is more preferably 50 mol % and the upper limit thereof is more preferably 89.9 mol %.

The polymerizable monomer having a phenyl group and a sulfonate (b) is not especially limited as long as it is a monomer capable of allowing a sulfonic group to be contained on a surface of a carrier particle obtained after the polymerization, and examples include styrene sulfonate, divinylbenzene sulfonate, o-methyl styrene sulfonate and p-methyl styrene sulfonate.

A salt used in this case is not also especially limited, and examples include a sodium salt, a potassium salt, a lithium salt and an ammonium salt.

One of these polymerizable monomers may be singly used, or two or more of them may be used in combination. Among these, styrene sulfonate is preferably used, and sodium styrene sulfonate is more preferably used.

The content of the polymerizable monomer having a phenyl group and a sulfonate (b) in the monomer mixture has a lower limit of preferably 0.01 mol % and an upper limit of preferably 5 mol %. If the content of the polymerizable monomer having a phenyl group and a sulfonate (b) is less than 0.01 mol %, the particle size may become too large, and if the content exceeds 5 mol %, the particle size distribution may become too wide in some cases. The lower limit of the content of the polymerizable monomer having a phenyl group and a sulfonate (b) is more preferably 0.05 mol %, and the upper limit thereof is more preferably 3 mol %.

The polymerizable monomer having a naphthyl group (c) is not especially limited, and examples include 1-vinylnaphthalene, 2-vinylnaphthalene, α-naphthyl (meth)acrylate and β-naphthyl (meth)acrylate. One of these polymerizable monomers may be singly used, or two or more of these may be used in combination. Among these, 1-vinylnaphthalene is preferably used.

The content of the polymerizable monomer having a naphthyl group (c) in the monomer mixture has a lower limit of preferably 5 mol % and an upper limit of preferably 59.9 mol %. If the content of the polymerizable monomer having a naphthyl group (c) is less than 5 mol %, high sensitivity may not be attained in some cases, and if the content exceeds 59.9 mol %, particles may not be formed by polymerization or the particle size distribution may become wide in some cases. The lower limit of the content of the polymerizable monomer having a naphthyl group (c) is more preferably 10 mol %, and the upper limit thereof is more preferably 49.9 mol %.

The monomer mixture may further comprise a polymerizable unsaturated monomer.

The polymerizable unsaturated monomer is not especially limited as long as it may be used for general radical polymerization, and examples include (meth)acrylic acid, (meth)acrylic ester, (meth)acrylonitrile, (meth)acrylamide, vinyl halide, vinyl ester, (meth)acrolein, a maleic acid derivative and a fumaric acid derivative.

It is noted that (meth)acrylic acid herein means acrylic acid or methacrylic acid.

In the case where the monomer mixture further comprises the polymerizable unsaturated monomer, the content of the polymerizable unsaturated monomer should be set so as not to impair the preferable contents of the polymerizable monomer having a phenyl group (a), the polymerizable monomer having a phenyl group and a sulfonate (b) and the polymerizable monomer having a naphthyl group (c).

In the case where the monomer mixture comprises the polymerizable unsaturated monomer, the content of the polymerizable unsaturated monomer has an upper limit of preferably 20 mol %. If the content of the polymerizable unsaturated monomer exceeds 20 mol %, high sensitivity may not be attained in some cases. The upper limit of the content of the polymerizable unsaturated monomer is more preferably 5 mol %.

A preferable lower limit of the content of the polymerizable unsaturated monomer is not especially limited but depends upon the properties to be controlled, such as hardness, elasticity and water resistance, of the latex particle, and may be appropriately set through, for example, an experiment.

The latex particle for a measurement reagent of the present invention is obtained by copolymerizing the monomer mixture. Here, it is extremely significant that a surfactant widely used as an emulsifier (for example, an alkali metal salt of alkyl benzene sulfonic acid) is not used in the copolymerization. If a surfactant is used, the surfactant remains in the resulting latex particle, and the remaining surfactant inhibits the antigen- or antibody-coating (immobilization) on the surface of the latex particle. Therefore, the amount of the antigen or the antibody adsorbed onto the latex particle is insufficient, and hence high measurement sensitivity cannot be attained.

As a method for the copolymerization, any of the conventionally known methods may be employed except that the copolymerization is performed in an aqueous medium without using a surfactant, and for example, the aforementioned monomer mixture and a polymerization initiator are put in a reaction vessel charged with an aqueous medium used as a solvent, so as to be heated under a nitrogen atmosphere with stirring.

The aqueous medium is a mixed solvent of water and a monovalent alcohol having 1 to 4 carbon atoms (hereinafter sometimes referred to as the "$C_{1-4}$ alcohol"), and contains the $C_{1-4}$ alcohol in a concentration of 7.5 to 25% by weight. Examples of the $C_{1-4}$ alcohol include linear alcohols such as methanol and ethanol; and branched chain alcohols such as isopropyl alcohol and t-butyl alcohol. Among these, ethanol is suitably used.

The concentration of the $C_{1-4}$ alcohol in the aqueous medium is in a range of 7.5 to 25% by weight. If the concentration of the $C_{1-4}$ alcohol is higher than 25% by weight, the particle size distribution becomes so wide that the particle size is varied. On the other hand, if the concentration of the $C_{1-4}$ alcohol is lower than 7.5% by weight, although the particle size is not widely distributed, high measurement sensitivity cannot be attained when such aqueous medium is used for the preparation of the latex particle for a measurement reagent. When the aqueous medium is used in a concentration within the aforementioned range, it is possible to produce an excellent latex particle for a measurement reagent in which spread of the particle size distribution is controlled to minimally vary the particle size and a sufficient amount of an antigen or an antibody may be adsorbed to attain high measurement sensitivity.

As the polymerization initiator, any of known radical initiators may be used. Specific examples include persulfates such as potassium persulfate, sodium persulfate and ammonium persulfate; azo compounds such as 2,2'-azobisisobutyronitrile, 2,2'-azobis(4-methoxy-2,4-dimethylvaleronitrile) and 2,2'-azobis-2,4-dimethylvaleronitrile; and organic peroxides such as benzoyl peroxide, di-t-butyl peroxide, lauroyl peroxide and t-butylperoxy-2-ethylhexanoate. Among these, persulfates are preferably used, and potassium persulfate is more preferably used.

The content of the polymerization initiator is not especially limited, and is generally 0.01 to 1% by weight based on the total amount of the polymerizable monomers.

In the copolymerization, a polymerization temperature is preferably 50 to 100° C. and more preferably 60 to 85° C. Besides, polymerization time depends upon the conditions such as the compositions and the concentrations of the polymerizable monomers and the used polymerization initiator, and is generally 5 to 50 hours.

The latex particles for a measurement reagent of the present invention produced in this manner are obtained in a state suspended in water or an aqueous solvent. The concentration of the latex particles for a measurement reagent in the suspension is not especially limited, and is preferably 1 to 20% by weight in general. If the concentration is less than 1% by weight, it is necessary to concentrate the suspension in preparing coated latex particles, and if it exceeds 20% by weight, the particles may be aggregated in some cases.

An average particle size of the latex particles for a measurement reagent of the present invention may be appropriately selected in accordance with a specific method of the latex immunoturbidimetric method, the specification of a used measuring device and the like, and has a lower limit of preferably 0.01 μm and an upper limit thereof of preferably 1.0 μm. If the average particle size is less than 0.01 μm, optical change caused by the aggregation may be too small to attain sensitivity necessary for measurement, or production cost may be increased because a longer period of time is necessary for centrifugation or the like in preparing coated latex particles. If the average particle size exceeds 1.0 μm, optical change caused by the aggregation of coated latex particles may be beyond a measurable range of an optical measuring device when the concentration of a test substance in a measurement sample is high, and hence, optical change caused in accordance with the amount of the test substance may not be obtained in some cases. The lower limit and the upper limit of the average particle size are respectively more preferably 0.05 μm and 0.7 μm, and further more preferably 0.1 μm and 0.4 μm.

A coefficient of variation (CV value) of the particle size of the latex particles for a measurement reagent of the present invention is preferably 10% or less. If the coefficient of variation (CV value) exceeds 10%, production reproducibility attained in preparing coated latex particles may be lowered, so as to degrade the performance (measurement reproducibility) of a resulting measurement reagent. The coefficient of variation (CV value) is more preferably 5% or less and further more preferably 3% or less. Incidentally, the coefficient of variation of the particle size is calculated in accordance with the following equation (1):

$$\text{Coefficient of variation (CV value) of particle size} = \text{standard deviation of particle size/average particle size} \qquad \text{Equation (1)}$$

As described above, the spread of the particle size distribution can be converged into a certain range in accordance with the concentration of the $C_{1-4}$ alcohol in the aqueous solvent employed in the copolymerization reaction. Those skilled in the art can appropriately select and use latex particles for a measurement reagent having a suitable coefficient of variation in consideration of the characteristics (physical properties, a concentration in a measurement sample and the like) of a test substance, the characteristics of an antigen or an antibody to be used for the coating of the latex particles, reproducibility between production lots and the like.

When the latex particle for a measurement reagent of the present invention is used as a carrier for carrying a substance specifically binding to a test substance, a coated latex particle can be produced.

The coated latex particle comprising the latex particle for a measurement reagent of the present invention carrying a substance specifically binding to a test substance is also another aspect of the present invention.

The substance specifically binding to a test substance is not especially limited as long as it is a biologically active substance usually used as a reagent for serum-immunological tests (one used in an immunological aggregation reaction or aggregation inhibition reaction) or used in biochemical measurement. Especially, a substance usable in an antigen-antibody reaction is suitably used.

In the present invention, examples of the substance usable as an antigen or antibody in an antigen-antibody reaction include protein, nucleic acid, nucleoprotein, hormone such as estrogen, lipid or the like.

Examples of the antigen include various antigens, receptors and enzymes. More specific examples include β2 microglobulin, C-reactive protein (CRP), human fibrinogen, ferritin, a rheumatoid factor (RA), α-fetoprotein (AFP), a mycoplasma antigen and an HBs antigen.

Examples of the antibody include antibodies against various toxins, infectious agents and the like. More specific examples include an anti-streptolysin O antibody, an anti-estrogen antibody, a β2 microglobulin antibody, a *Treponema pallidum* antibody, an antibody against syphilis lipid antigen, an anti-HBs antibody, an anti-HBc antibody, an anti-Hbe antibody, an anti-PSA antibody and an anti-CRP antibody.

Incidentally, the antibody to be carried on the latex particle for a measurement reagent for producing the coated latex particle may be not only an immunoglobulin molecule itself but also a fragment such as an F(ab')$_2$. Furthermore, the antibody may be either a polyclonal antibody or a monoclonal antibody.

The antibody can be obtained by a generally employed method.

The terms of "antigen-antibody reaction", "antigen" and "antibody" used herein have the general meanings as well as may connote, in some cases, the aforementioned concept and form that coated latex particles may be aggregated through a specific binding reaction, and hence, these terms are not to be restrictively understood.

A method for producing a coated latex particle by allowing the latex particle for a measurement reagent of the present invention to carry a substance specifically binding to a test substance is not especially limited, and any of conventionally known carrying methods via physical and/or chemical bond may be employed.

The amount of a substance specifically binding to a test substance to be carried on the coated latex particle of the present invention depends upon the type of the substance specifically binding to a test substance to be used, and may be experimentally set appropriately to an optimum amount.

Incidentally, the terms "carry", "coat" and "immobilize" herein have the general meanings and are used in substantially the same meanings.

The coated latex particle of the present invention obtained in this manner is subjected to a coating (blocking) treatment with bovine serum albumin or the like if necessary and dispersed in an appropriate buffer solution to be used as a coated latex particle dispersion. The coated latex particle dispersion may be used as a measurement reagent for the immunoturbidimetric method.

The measurement reagent for immunoturbidimetric method comprising the coated latex particle of the present invention dispersed in a buffer solution is also another aspect of the present invention.

The measurement reagent for immunoturbidimetric method of the present invention can be combined with a diluent (buffer solution), a standard substance and the like used for measurement, so as to be used as a measurement reagent kit.

The diluent is used for diluting a measurement sample or the like.

As the diluent, any of buffer solutions of pH 5.0 to 9.0 may be used. Specific examples include a phosphate buffer, a glycine buffer, a Tris buffer, a borate buffer, a citrate buffer and a Good's buffer.

The measurement reagent and the diluent for immunoturbidimetric method of the preset invention may contain various sensitizers for purpose of improving the measurement sensitivity and accelerating an antigen-antibody reaction.

Examples of the sensitizers include alkylated polysaccharides such as methyl cellulose and ethyl cellulose, pullulan and polyvinylpyrrolidone.

The measurement reagent and the diluent for immunoturbidimetric method of the present invention may contain: protein such as albumin (bovine serum albumin or egg albumin), casein, gelatin or a hydrolysate thereof; an amino acid; a surfactant; or the like for purpose of inhibiting a non-specific aggregation reaction caused by a substance other than a test substance present in a measurement sample, or improving the stability of the measurement reagent.

When the measurement reagent for immunoturbidimetric method of the present invention is used, the amount of a test substance contained in a measurement sample can be measured by optically measuring the degree of aggregation of coated latex particles caused through a reaction between the test substance contained in the measurement sample and a substance specifically binding to the test substance carried on the coated latex particles.

For optically measuring the degree of aggregation, an optical device capable of detecting the intensity of scattered light, the intensity of transmitted light, absorbance or the like, or an optical device provided with a plurality of detection methods for these can be used. Typically, any of biochemical autoanalyzers widely used for clinical laboratory tests may be used.

As a method for optically measuring the degree of aggregation, any of conventionally known methods may be employed, and examples of the method include nephelometry in which the formation of aggregation is detected by increase of the turbidity, a method in which the formation of aggregation is detected by change of a particle size distribution or an average particle size, and an integrating sphere turbidity method in which change of forward scattered light caused by the formation of aggregation is measured by using an integrating sphere for comparing with a ratio to the intensity of transmitted light.

Furthermore, examples of a method of measurement include a rate test (rate assay) in which at least two measured values are obtained at different points of time so as to obtain the degree of aggregation on the basis of increment (an increase rate) of the measured value caused between these points of time, and an end point test (end point assay) in which one measured value is obtained at one point of time (a point of time regarded as an end point of a reaction in general) so as to obtain the degree of aggregation on the basis of the measured value. Among these, the end point test by the nephelometry is suitably employed because the measurement can be easily and rapidly performed.

The terms of "immunoturbidimetric" and "immunoturbidimetric method" used herein connote all the aforementioned concepts and forms, and these terms are not to be restrictively understood.

Advantageous Effects of Invention

The present invention can provide a latex particle for a measurement reagent with which highly sensitive measurement can be performed even on a measurement sample containing a test substance in a dilute concentration.

The latex particle for a measurement reagent of the present invention can be improved in measurement sensitivity for a test substance in a dilute concentration region with a particle size kept at the same level as the conventional polystyrene latex particles and without reducing the amount of protein to be adsorbed. Furthermore, when the latex particle for a measurement reagent of the present invention is used, a highly sensitive measurement reagent free from degradation of the storage stability of the measurement reagent through particle precipitation can be obtained.

BRIEF DESCRIPTION OF DRAWINGS

FIG. 2 illustrates sensitive curves (analytical curves) obtained by measuring a CRP antigen standard solution by using latex particles for a measurement reagent produced in Examples 1 to 5 and Comparative Examples 1 to 5, in which FIG. 2(a) illustrates the whole measured concentration region and FIG. 2(b) enlargedly illustrates the sensitivity curves in a concentration region of 0.6 mg/dL or less.

DESCRIPTION OF EMBODIMENTS

Figure 1:
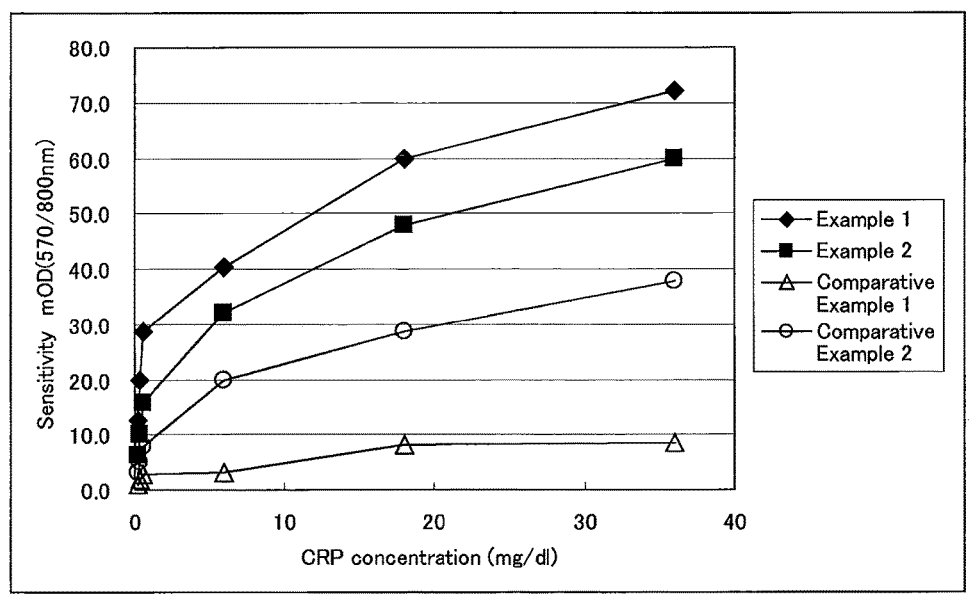
FIG. 1 illustrates sensitivity curves (analytical curves) obtained by measuring a CRP antigen standard solution by using latex particles for a measurement reagent produced in Examples 1 and 2 and Comparative Examples 1 and 2.

The present invention will now be described in more details with reference to examples, but it is noted that the present invention is not limited to these examples.

Example 1

A glass reaction vessel (having a volume of 1 L) equipped with a stirrer, a reflux condenser, a temperature detector, a nitrogen introducing tube and a jacket was charged with 400 g of ultrapure water, 100 g of ethanol, 19 g of a styrene monomer, 25 g of 1-vinylnaphthalene, 0.01 g of sodium styrene sulfonate and 0.15 g of potassium persulfate, and after substituting the inside of the vessel by a nitrogen gas, polymerization was performed for 24 hours with stirring at 70° C. and at a rate of 160 rpm.

After the polymerization was completed, the resulting solution was subjected to a filtering treatment with a paper filter, thereby taking out latex particles. Thereafter, the latex particles were subjected to a dialysis treatment with a dialysis membrane for 48 hours, and thus, refined latex particles for a measurement reagent were obtained. The thus obtained latex particles had an average particle size of 0.351 μm and a CV value of the particle size of 3.8%.

Incidentally, the particle size and the CV value of the latex particles were obtained by the following method: The latex particles were placed on a collodion membrane by a usual method, an image of the particles was captured by using a transmission electron microscope, and particle sizes of 100 or more particles observed in the image were measured.

Example 2

Latex particles for a measurement reagent were obtained in the same manner as in Example 1 except that 450 g of ultrapure water, 50 g of ethanol, 35 g of a styrene monomer, 20 g of 1-vinylnaphthalene, 0.01 g of sodium styrene sulfonate and 0.18 g of potassium persulfate were used instead of "400 g of ultrapure water, 100 g of ethanol, 19 g of a styrene monomer, 25 g of 1-vinylnaphthalene, 0.01 g of sodium styrene sulfonate and 0.15 g of potassium persulfate".

The thus obtained latex particles had an average particle size of 0.355 μm and a CV value of the particle size of 2.2%.

Comparative Example 1

Latex particles for a measurement reagent were obtained in the same manner as in Example 1 except that 200 g of ultrapure water, 200 g of ethanol, 12 g of a styrene monomer, 18 g of 1-vinylnaphthalene, 0.30 g of potassium persulfate and 0.06 g of sodium dodecylbenzenesulfonate (a surfactant) were used instead of "400 g of ultrapure water, 100 g of ethanol, 19 g of a styrene monomer, 25 g of 1-vinylnaphthalene, 0.01 g of sodium styrene sulfonate and 0.15 g of potassium persulfate".

The thus obtained latex particles had an average particle size of 0.433 μm and a CV value of the particle size of 15.0%.

The latex particles of this comparative example correspond to the latex particles described in Patent Literature 2.

Comparative Example 2

Latex particles for a measurement reagent were obtained in the same manner as in Example 1 except that 500 g of ultrapure water, 45 g of a styrene monomer, 0.01 g of sodium styrene sulfonate and 0.15 g of potassium persulfate were used instead of "400 g of ultrapure water, 100 g of ethanol, 19 g of a styrene monomer, 25 g of 1-vinylnaphthalene, 0.01 g of sodium styrene sulfonate and 0.15 g of potassium persulfate".

The thus obtained latex particles had an average particle size of 0.405 μm and a CV value of the particle size of 3.3%.

The latex particles of this comparative example correspond to the latex particles described in Patent Literature 1.

(Evaluation 1)

(1) Evaluation of Protein Adsorption Amount of Latex Particles for Measurement Reagent The latex particles for a measurement reagent produced in each of Examples 1 and 2 and Comparative Examples 1 and 2 were mixed with BSA and a phosphate buffer (pH 7.4) so as to attain final concentrations of latex particles of 0.4% by weight (4 mg as an amount of a solid), BSA of 0.8 mg/mL and phosphate buffer solution of 20 mmol/L, and the resulting mixture was shook by using a wave rotor (50 rpm) for 3 hours in a cold room of 4° C., thereby causing the BSA to be adsorbed onto the latex particles. Thereafter, the resulting solution was centrifuged (12000 rpm, 30 minutes, 15° C.), a supernatant was dispensed, and a protein concentration in the supernatant was measured by using an A/G test kit Wako (manufactured by Wako Pure Chemical Industries, Ltd.). The protein concentration in the supernatant was subtracted from a protein concentration in a negative control (with no latex particles contained), thereby calculating a protein binding amount adsorbed onto the latex particles (a BSA binding amount per unit area of the latex particles).

The results are shown in Table 1.

TABLE 1

| | Example 1 | Example 2 | Example 3 | Example 4 | Example 5 | Comparative Example 1 | Comparative Example 2 | Comparative Example 3 | Comparative Example 4 | Comparative Example 5 |
|---|---|---|---|---|---|---|---|---|---|---|
| Ultrapure water (g) | 400 | 450 | 375 | 400 | 462.5 | 200 | 500 | 250 | 350 | 475 |
| Ethanol (g) | 100 | 50 | 125 | 100 | 37.5 | 200 | 0 | 250 | 150 | 25 |
| Styrene (g) | 19 | 35 | 35 | 35 | 35 | 12 | 45 | 35 | 35 | 35 |
| 1-vinylnaphthalene (g) | 25 | 20 | 20 | 20 | 20 | 18 | 0 | 20 | 20 | 20 |
| Sodium styrene sulfonate (g) | 0.01 | 0.01 | 0.01 | 0.01 | 0.01 | 0 | 0.01 | 0.01 | 0.01 | 0.01 |
| Potassium persulfate (g) | 0.15 | 0.18 | 0.18 | 0.18 | 0.18 | 0.3 | 0.15 | 0.18 | 0.18 | 0.18 |

TABLE 1-continued

|  | Example 1 | Example 2 | Example 3 | Example 4 | Example 5 | Comparative Example 1 | Comparative Example 2 | Comparative Example 3 | Comparative Example 4 | Comparative Example 5 |
|---|---|---|---|---|---|---|---|---|---|---|
| Sodium dodecylbenzenesulfonate (g) | 0 | 0 | 0 | 0 | 0 | 0.06 | 0 | 0 | 0 | 0 |
| Ethanol concentration (% by weight) | 20 | 10 | 25 | 20 | 7.5 | 50 | 0 | 50 | 30 | 5 |
| Particle size (μm) | 0.351 | 0.355 | 0.361 | 0.359 | 0.345 | 0.433 | 0.405 | 0.401 | 0.368 | 0.343 |
| CV value of particle size(%) | 3.8 | 2.2 | 7.8 | 4.1 | 3.1 | 15 | 3.3 | 17.1 | 13 | 2.8 |
| BSA binding amount (mg/m$^2$) | 3.16 | 3.33 | 3.11 | 3.22 | 3.05 | 1.52 | 3.61 | 3.28 | 3.16 | 3.04 |

It is understood from Table 1 that the amount of BSA adsorbed is extremely small in using the latex particles for a measurement reagent of Comparative Example 1 as compared with that attained in using the latex particles of Examples 1 and 2 and Comparative Example 2. On the other hand, the latex particles for a measurement reagent of Examples 1 and 2 showed the amount of BSA adsorbed equivalent to that of the latex particles for a measurement reagent of Comparative Example 2.

Based on these results, it was confirmed that the latex particles for a measurement reagent of the present invention can adsorb a large amount of antibody or the like useful for constructing a measurement reagent for the immunoturbidimetric method as compared with the latex particles for a measurement reagent of Comparative Example 1 produced by using a surfactant.

(2) Evaluation of Measurement Sensitivity of Measurement Reagent Using Coated Latex Particles After the latex particles for a measurement reagent produced in each of Examples 1 and 2 and Comparative Examples 1 and 2 were centrifugally refined, an anti-CRP antibody was coated on latex particles.

The thus obtained antibody coated latex particles were subjected to three centrifugal washing with a buffer solution containing 0.1% BSA and then subjected to a blocking treatment. Subsequently, the concentration of the antibody coated latex particles was adjusted to 0.025% by weight with a buffer solution, thereby making a measurement reagent (second reagent) containing the antibody coated latex particles.

The thus obtained measurement reagents were used for measuring a CRP antigen standard solution, thereby obtaining sensitivity curves (analytical curves).

The obtained sensitivity curves are shown in FIG. 1.
Measurement conditions were as follows:
(Measurement Conditions A)
Apparatus: Hitachi 7170 autoanalyzer
Wavelength: 570 nm/800 nm
Photometric point: 18-34 (end point assay)
Measurement temperature: 37° C.
Measurement sample (CRP standard solutions of 0-36 mg/dL): 2 uL
CRP concentrations in respective CRP standard solutions: 0.2, 0.3, 0.6, 6, 18, 36 mg/dL
First reagent: Nanopia (registered trademark) CRP buffer solution 100 μL
Second reagent: 100 μL The measurement was performed by an end point assay as follows: A measurement sample and the first reagent were mixed and stirred, the second reagent was further added thereto, and the resulting solution was mixed and stirred. After a certain period of time, the turbidity was measured.

Referring to FIG. 1, the measurement reagent using the antibody coated latex particles prepared from the latex particles for a measurement reagent of Comparative Example 1 (using a surfactant in the copolymerization) could not attain substantial sensitivity at a CRP concentration of 0.6 mg/dL or less and also could not attain sufficient sensitivity differences between the respective concentrations when the CRP concentration was 6 mg/mL or more.

On the other hand, the measurement reagent using the antibody coated latex particles prepared from the latex particles for a measurement reagent of Comparative Example 2 (not containing a polymerizable monomer having a naphthyl group) showed remarkably improved sensitivity at a concentration of 6 mg/dL as compared with that of Comparative Example 1 but could attain sensitivity merely slightly improved at a concentration of 0.6 mg/dL or less as compared with that of Comparative Example 1.

On the contrary, the measurement reagents using the antibody coated latex particles prepared from the latex particles for a measurement reagent of Examples 1 and 2 both showed remarkably improved sensitivity at any CRP concentration as compared with those of Comparative Examples 1 and 2. In particular, the sensitivity was clearly improved at a concentration of 0.6 mg/dL or less where substantial sensitivity could not be attained by those of Comparative Examples 1 and 2. It was thus confirmed that the sensitivity can be improved in Examples 1 and 2 even though the amount of protein adsorbed is equivalent to that attained in Comparative Example 2.

Example 3

Latex particles for a measurement reagent were obtained in the same manner as in Example 1 except that 375 g of ultrapure water, 125 g of ethanol, 35 g of a styrene monomer, 20 g of 1-vinylnaphthalene, 0.01 g of sodium styrene sulfonate and 0.18 g of potassium persulfate were used instead of "400 g of ultrapure water, 100 g of ethanol, 19 g of a styrene monomer, 25 g of 1-vinylnaphthalene, 0.01 g of sodium styrene sulfonate and 0.15 g of potassium persulfate".

The thus obtained latex particles had an average particle size of 0.361 μm and a CV value of the particle size of 7.8%.

Example 4

Latex particles for a measurement reagent were obtained in the same manner as in Example 1 except that 400 g of ultrapure water, 100 g of ethanol, 35 g of a styrene monomer, 20 g of 1-vinylnaphthalene, 0.01 g of sodium styrene sulfonate and 0.18 g of potassium persulfate were used instead of "400 g of ultrapure water, 100 g of ethanol, 19 g of a styrene monomer, 25 g of 1-vinyl naphthalene, 0.01 g of sodium styrene sulfonate and 0.15 g of potassium persulfate".

The thus obtained latex particles had an average particle size of 0.359 μm and a CV value of the particle size of 4.1%.

Example 5

Latex particles for a measurement reagent were obtained in the same manner as in Example 1 except that 462.5 g of ultrapure water, 37.5 g of ethanol, 35 g of a styrene monomer, 20 g of 1-vinylnaphthalene, 0.01 g of sodium styrene sulfonate and 0.18 g of potassium persulfate were used instead of "400 g of ultrapure water, 100 g of ethanol, 19 g of a styrene monomer, 25 g of 1-vinyl naphthalene, 0.01 g of sodium styrene sulfonate and 0.15 g of potassium persulfate".

The thus obtained latex particles had an average particle size of 0.345 μm and a CV value of the particle size of 3.1%.

Comparative Example 3

Latex particles for a measurement reagent were obtained in the same manner as in Example 1 except that 250 g of ultrapure water, 250 g of ethanol, 35 g of a styrene monomer, 20 g of 1-vinylnaphthalene, 0.01 g of sodium styrene sulfonate and 0.18 g of potassium persulfate were used instead of "400 g of ultrapure water, 100 g of ethanol, 19 g of a styrene monomer, 25 g of 1-vinyl naphthalene, 0.01 g of sodium styrene sulfonate and 0.15 g of potassium persulfate".

The thus obtained latex particles had an average particle size of 0.401 μm and a CV value of the particle size of 17.1%.

Comparative Example 4

Latex particles for a measurement reagent were obtained in the same manner as in Example 1 except that 350 g of ultrapure water, 150 g of ethanol, 35 g of a styrene monomer, 20 g of 1-vinylnaphthalene, 0.01 g of sodium styrene sulfonate and 0.18 g of potassium persulfate were used instead of "400 g of ultrapure water, 100 g of ethanol, 19 g of a styrene monomer, 25 g of 1-vinyl naphthalene, 0.01 g of sodium styrene sulfonate and 0.15 g of potassium persulfate".

The thus obtained latex particles had an average particle size of 0.368 μm and a CV value of the particle size of 13.0%.

Comparative Example 5

Latex particles for a measurement reagent were obtained in the same manner as in Example 1 except that 475 g of ultrapure water, 25 g of ethanol, 35 g of a styrene monomer, 20 g of 1-vinylnaphthalene, 0.01 g of sodium styrene sulfonate and 0.18 g of potassium persulfate were used instead of "400 g of ultrapure water, 100 g of ethanol, 19 g of a styrene monomer, 25 g of 1-vinyl naphthalene, 0.01 g of sodium styrene sulfonate and 0.15 g of potassium persulfate".

The thus obtained latex particles had an average particle size of 0.343 μm and a CV value of the particle size of 2.8%.

(Evaluation 2)

(1) Evaluation of Protein Adsorption Amount of Latex Particles for Measurement Reagent The latex particles for a measurement reagent produced in each of Examples 3 to 5 and Comparative Examples 3 to 5 were used for calculating the binding amount of protein adsorbed onto the latex particles (a BSA binding amount of per unit area of the latex particles) through the same operation and by the same method as described above in the item "(1) Evaluation of protein adsorption amount of latex particles for measurement reagent" of "Evaluation 1".

The results are shown in Table 1.

(2) Evaluation of Sensitivity of Measurement Reagent Using Latex Particles

The latex particles for a measurement reagent produced in each of Examples 3 to 5 and Comparative Examples 3 to 5 were used for making a measurement reagent containing the latex particles for a measurement reagent of each of Examples 3 to 5 and Comparative Examples 3 to 5 through the same operation and by the same method as described above in the item "(2) Evaluation of measurement sensitivity of measurement reagent using latex particles" of "Evaluation 1".

The thus obtained measurement reagents were used for measuring a CRP antigen standard solution under the aforementioned measurement conditions A so as to obtain sensitivity curves (analytical curves).

Figure 2:
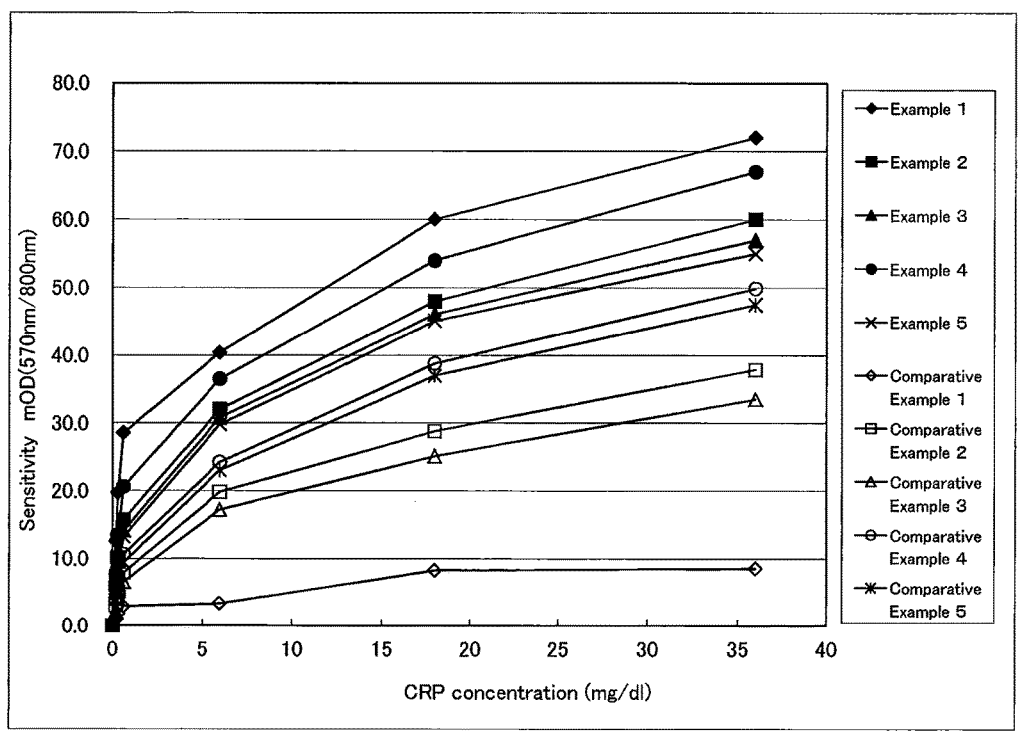
Figure 2:
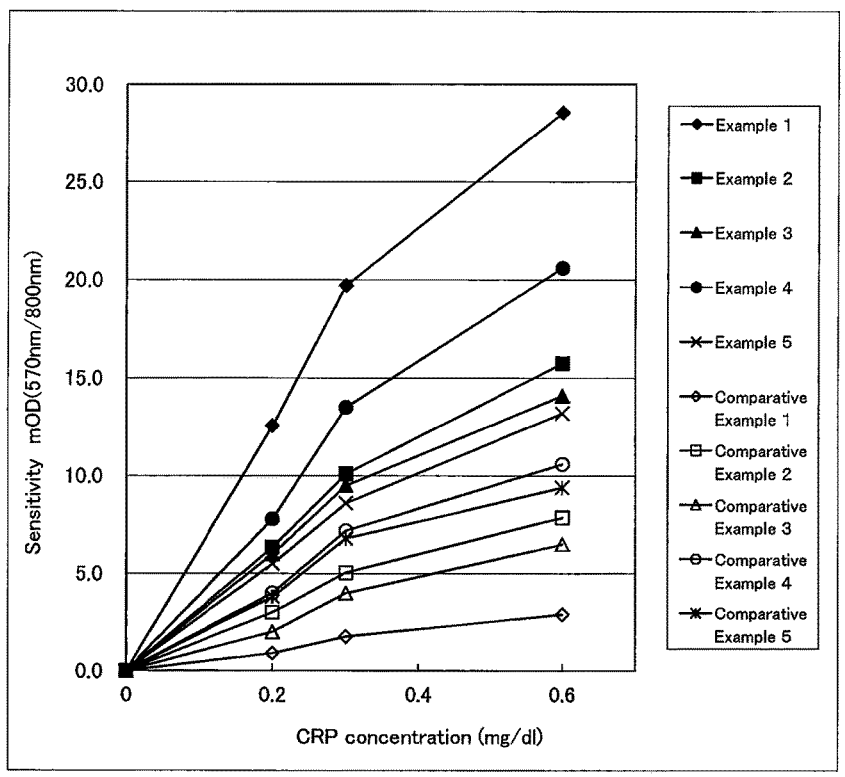

The obtained sensitivity curves are shown in FIG. 2, and measured absorbances are shown in Table 2.

Incidentally, the results obtained in Examples 1 and 2 and Comparative Examples 1 and 2 described above are also shown in FIG. 2 and Table 2.

TABLE 2

| CRP concentration in CRP standard solution (mg/dL) | Absorbance(mOD) (Wavelength 570 nm/800 nm) | | | | | | | | | |
|---|---|---|---|---|---|---|---|---|---|---|
| | Example 1 | Example 2 | Example 3 | Example 4 | Example 5 | Comparative Example 1 | Comparative Example 2 | Comparative Example 3 | Comparative Example 4 | Comparative Example 5 |
| 0 | 0.0 | 0.0 | 0.0 | 0.0 | 0.0 | 0.0 | 0.0 | 0.0 | 0.0 | 0.0 |
| 0.2 | 12.6 | 6.4 | 6.0 | 7.8 | 5.5 | 0.9 | 3.0 | 2.0 | 4.0 | 3.8 |
| 0.3 | 19.7 | 10.1 | 9.5 | 13.5 | 8.6 | 1.8 | 5.1 | 4.0 | 7.2 | 6.8 |
| 0.6 | 28.6 | 15.8 | 14.1 | 20.6 | 13.2 | 2.9 | 7.9 | 6.5 | 10.6 | 9.4 |
| 6 | 40.4 | 32.0 | 30.8 | 36.5 | 29.8 | 3.3 | 19.8 | 17.2 | 24.2 | 23.0 |
| 18 | 60.0 | 48.0 | 46.1 | 54.0 | 45.1 | 8.3 | 28.8 | 25.1 | 38.8 | 37.0 |
| 36 | 72.0 | 60.0 | 57.0 | 67.0 | 55.0 | 8.5 | 37.9 | 33.5 | 49.9 | 47.5 |

Note:
All results are values after blank reduction.

Referring to Table 1, the latex particles produced in Comparative Examples 1 and 3 (where an ethanol concentration was 50%) and Comparative Example 4 (where the same was 30%) had CV values exceeding 10% differently from the latex particles produced in Examples 1 and 4 (where the same was 20%), Example 2 (where the same was 10%), Example 3 (where the same was 25%), Example 5

(where the same was 7.5%) and Comparative Example 5 (where the same was 5%). It is found based on these results that the CV value is varied so as to largely vary the particle size of the obtained latex particles for a measurement reagent when the ethanol concentration is higher beyond the preferable concentration range of the present invention. Furthermore, the latex particles produced in Comparative Example 2 (where the same was 0%) and Comparative Example 5 (where the same was 5%) had CV values equivalent to those of the latex particles of Examples (as shown in Table 1) but measurement sensitivity shown by the measurement reagents obtained by using them was insufficient and lower than that shown by the measurement reagents obtained by using the latex particles of Examples. The measurement sensitivity was found to be insufficient and lower also in Comparative Examples 1, 3 and 4 than that of the measurement reagents obtained by using the latex particles of Examples (as shown in FIG. 2 and Table 2).

Incidentally, the amount of BSA adsorbed was substantially the same in the respective examples and comparative examples except for Comparative Example 1 using a surfactant in the copolymerization (as shown in Table 1).

It was confirmed, based on Table 1, that the latex particles for a measurement reagent of Examples 3 to 5 are equivalent to the latex particles for a measurement reagent of Comparative Examples 3 to 5 in the amount of BSA adsorbed.

As described so far, it was confirmed that a latex particle for a measurement reagent with which highly sensitive measurement can be performed even on a measurement sample containing a test substance in a dilute concentration can be produced according to the present invention.

Furthermore, it was confirmed that the latex particle for a measurement reagent of the present invention can be improved in the measurement sensitivity to a test substance in a dilute concentration region without reducing an amount of protein adsorbed with the particle size kept at the same level as the conventional polystyrene latex particles.

Moreover, it was confirmed that the latex particle for a measurement reagent of the present invention has a particle size distribution converged to a CV value of 10% or less, and since the variation in the particle size is thus small, the production reproducibility in preparing a coated latex particle is stabilized, resulting in also stabilizing the performance (measurement reproducibility) of a measurement reagent using it.

INDUSTRIAL APPLICABILITY

The present invention can provide a latex particle for a measurement reagent with which highly sensitive measurement can be performed even in measuring a measurement sample containing a test substance in a dilute concentration.

The invention claimed is:

1. A latex particle for a measurement reagent, comprising a copolymer having segments obtained by copolymerizing the following polymerizable monomers (a), (b) and (c):
    (a) at least one polymerizable monomer having a phenyl group selected from the group consisting of styrene, o-methyl styrene, p-methyl styrene, p-chlorostyrene, 4-vinylbenzoate, divinylbenzene and vinyl toluene;
    (b) at least one polymerizable monomer having a phenyl group and a sulfonate selected from the group consisting of styrene sulfonate, divinylbenzene sulfonate, o-methyl styrene sulfonate and p-methyl styrene sulfonate; and
    (c) at least one polymerizable monomer having a naphthyl group selected from the group consisting of 1-vinylnaphthalene and 2-vinylnaphthalene;
    wherein the latex particle contains not surfactants,
    wherein the copolymer is obtained by copolymerizing the polymerizable monomers in an aqueous medium containing 7.5 to 25% by weight of a $C_{1-4}$ alcohol without using any surfactants, and
    wherein the latex particle has an average particle size of 0.01 to 1.0 μm and a coefficient of variation of the particle size of 10% or less.

2. The latex particle for a measurement reagent according to claim 1,
    wherein the $C_{1-4}$ alcohol is ethanol.

3. The latex particle for a measurement reagent according to claim 1,
    wherein the monomer mixture comprises a polymerizable unsaturated monomer.

4. The latex particle for a measurement reagent according to claim 1,
    wherein:
    the polymerizable monomer (a) is styrene,
    the polymerizable monomer (b) is styrene sulfonate, and
    the polymerizable monomer (c) is 1-vinylnaphthalene.

5. A coated latex particle comprising the latex particle according to claim 1 wherein the latex particle carries a substance specifically binding to a test substance.

6. A measurement reagent for immunoturbidimetric method, comprising the coated latex particle according to claim 5 dispersed in a buffer solution.

* * * * *